(12) United States Patent (10) Patent No.: US 12,429,476 B2
Pérez Díaz et al. (45) Date of Patent: Sep. 30, 2025

(54) METHOD AND SYSTEM FOR REAL-TIME DETECTION OF BIOLOGICAL AGENTS SUSPENDED IN THE AIR

(71) Applicants: Counterfog SL, Madrid (ES); San Jorge Tecnológicas SL, Madrid (ES)

(72) Inventors: José Luis Pérez Díaz, Madrid (ES); Juan Sánchez García-Casarrubios, Madrid (ES); Javier Corella Romero, Madrid (ES)

(73) Assignees: Counterfog SL, Madrid (ES); San Jorge Tecnológicas SL, Madrid (ES)

( * ) Notice: Subject to any disclaimer, the term of this patent is extended or adjusted under 35 U.S.C. 154(b) by 420 days.

(21) Appl. No.: 18/074,764

(22) Filed: Dec. 5, 2022

(65) Prior Publication Data

US 2023/0104599 A1 Apr. 6, 2023

Related U.S. Application Data

(63) Continuation of application No. PCT/ES2021/070382, filed on May 27, 2021.

(30) Foreign Application Priority Data

Jun. 5, 2020 (ES) ................ ES202030541

(51) Int. Cl.
*G01N 33/497* (2006.01)
*G01N 15/0205* (2024.01)
*G01N 21/53* (2006.01)

(52) U.S. Cl.
CPC ....... *G01N 33/497* (2013.01); *G01N 15/0211* (2013.01); *G01N 21/532* (2013.01)

(58) Field of Classification Search
CPC .... G01N 15/01; G01N 15/0211; G01N 15/06; G01N 15/075; G01N 2015/0038;
(Continued)

(56) References Cited

U.S. PATENT DOCUMENTS 4,762,413 A 8/1988 Namba et al.
5,229,839 A * 7/1993 Hayashi ............. G01N 15/0205
356/336

(Continued)

OTHER PUBLICATIONS

International Search Report, PCT/ES2021/070382, Aug. 16, 2021, 6 pages.

*Primary Examiner* — John E Breene
*Assistant Examiner* — Truong D Phan
(74) *Attorney, Agent, or Firm* — Edell, Shapiro & Finnan, LLC (57) ABSTRACT

Methods and apparatus for detecting biological agents suspended in air in real time. A method includes emitting towards an air sample a beam of monochromatic polarized light whose wavelength corresponds to an absorption maximum of a biological molecule. The method further includes receiving, at different scattering angles, the scattered light beam after passing through the sample and determining that there are particles in the sample that contain the biological molecules of interest if the intensity of the scattered light has a substantially higher peak than the rest of the scattered light. The amount of the biological molecules is then estimated according to the amplitude of the peak. The size of the particles containing the biological molecules is also estimated as a function of the scattering angle where the peak was detected.

20 Claims, 4 Drawing Sheets

(58) Field of Classification Search
CPC ... G01N 2021/4711; G01N 2021/4792; G01N 21/53; G01N 21/532; G01N 33/0004; G01N 33/497; G01N 15/0205; G01N 2015/0046; G01N 15/02; G01N 15/0272; G01N 21/9036; G01N 2291/103; G01N 2291/105; G08B 17/103; G08B 17/107; G08B 17/113
USPC ......... 73/23.3; 356/335, 336, 337, 340, 343, 356/331, 333
See application file for complete search history.

(56) References Cited

U.S. PATENT DOCUMENTS

| | | | |
|---|---|---|---|
| 5,902,385 | A | 5/1999 | Willeke et al. |
| 5,958,694 | A * | 9/1999 | Nikiforov ........ G01N 27/44791 216/33 |
| 6,011,621 | A | 1/2000 | Marijnissen et al. |
| 7,436,515 | B2 * | 10/2008 | Kaye .................... G01N 21/645 356/441 |
| 2011/0181869 | A1 | 7/2011 | Yamaguchi et al. |
| 2013/0217029 | A1 | 8/2013 | Sislian et al. |
| 2016/0202163 | A1 * | 7/2016 | Weissleder ....... G01N 33/57407 506/9 |
| 2020/0271559 | A1 * | 8/2020 | Cooper .................. G08B 17/10 |

* cited by examiner

METHOD AND SYSTEM FOR REAL-TIME DETECTION OF BIOLOGICAL AGENTS SUSPENDED IN THE AIR

CROSS-REFERENCE TO RELATED APPLICATIONS

This application relates to and claims the benefit and priority to International Application No. PCT/ES2021/070382, filed May 27, 2021, which claims the benefit and priority to Spanish Application No. P202030541, filed Jun. 5, 2020.

FIELD

The invention is in the field of detection of contamination formed by air-borne biological agents. In particular, the invention relates to a method capable of detecting very small air-borne biological agents suspended in the air, such as particles of the SARS-CoV-2 virus.

BACKGROUND

It is known that various infectious diseases, such as anthrax, tuberculosis or SARS-CoV-1 and SARS-Cov-2, are transmitted through the air. Particles of these pathogenic agents, either alone or combined with droplets or other particles, can remain floating in the air for hours, thus constituting a significant threat to human health. For this reason, procedures capable of analyzing the air to detect this type of pathogenic agents are currently necessary.

Currently, all airborne virus detection techniques are based on impactors and precipitators for taking a sample of particles on gelatin filters or in liquid suspension, these particles being subsequently cultured and (or analyzed. For example, the article by D. Verreault et al entitled "*Methods for sampling of Airborne Viruses*", Microbiol Mol Biol Rev. 2008 September; 72(3): 413-444, describes such a technique. There are also other techniques based on the precipitation of aerosols by vortex, as described in U.S. Pat. No. 5,902,385.

Although effective, these procedures turn out to be excessively slow for many of the most relevant applications. For example, they may require a time of about at least half an hour of sampling to increase the amount or concentration collected, and about at least another hour of analysis.

Another inconvenient of this type of procedure is that the smallest agents, such as the SARS-CoV-2 virus, which is no more than 120 nm, are more difficult to capture or impact because they flow with the air. In this way, impactors that are useful for capturing bacteria, fungi or yeasts are not capable of capturing smaller viruses.

SUMMARY

The present invention describes a method for real-time detection of biological agents suspended in the air. This procedure can be used both for monitoring ambient air and for diagnosing or detecting the presence of viruses, spores and/or other microorganisms in the air exhaled by a person. In addition, it is a procedure capable of detecting the presence of biological particles of micrometric size or even smaller, even detecting biological particles smaller than 2.5 micrometers. This is especially relevant, since these very small particles can penetrate the respiratory system as far as the alveoli. Therefore, the method of the invention is useful both in the medical field, for the diagnosis of the presence of viruses or other agents, and in the field of biological safety, for example for the detection of infectious people.

In this document, the term "particle" refers to any of drops, droplets, microorganisms, dust, biological agents such as viruses, and in general to any type of organic or inorganic particle that can be found suspended in the air, either solid, liquid, or biological.

A first aspect of the present invention is directed to a method for detecting biological agents suspended in the air in real time, which basically comprises the following steps 1. Emitting towards a test zone comprising an air sample a monochromatic polarized light beam whose wavelength corresponds essentially to an absorption maximum of a biological molecule of interest.

According to one embodiment, the wavelength of the emitted monochromatic polarized light beam ranges from 240 nm to 280 nm. This range of wavelengths includes the intervals of greatest absorption of very characteristic biological molecules, such as nucleotides, DNA, RNA, various amino acids, etc. For example, setting the wavelength to range from approximately 255 nm to 260 nm would allow the presence of nucleotides to be detected in the analyzed air.

In principle, the monochromatic polarized light beam could be of any type as long as it meets the aforementioned requirements, although a laser beam is preferably used.

2. Receiving in different positions corresponding to different scattering angles, the scattered light beam after passing through the air sample.

The monochromatic polarized light beam passes through the air sample present in the test area and, after Mie scattering, is received by photodetectors located in positions corresponding to the different possible scattering angles.

The main concept of the present invention is based on the fact that this dispersion is different depending on whether or not the particles suspended in the air contain biological molecules that have an absorption maximum essentially at the wavelength of the emitted monochromatic polarized light beam. If there are particles in the air sample that contain such biological molecules, there is an increase in the dispersion of the emitted beam in relation to the case in which they do not contain them. In addition, it has been discovered that the dispersion occurs preferentially at certain angles that depend on the size of the particles that contain the biological molecules. This information is used in the following steps to determine if there are particles in the air that contain biological molecules, as well as to estimate the number of biological molecules and the size of the particles that contain them.

As mentioned above, the presence of biological molecules in the tested air will cause polarized light passing through the test zone to be scattered to a much greater extent than if no biological molecules are present. Therefore, based on the presence or not of a scattered light peak received by the photodetectors, it is determined whether the analyzed air contains biological molecules. Since pathogenic and infectious biological agents, such as viruses, have a high content of biological molecules such as DNA, RNA, nucleotides, or amino acids, this makes it possible to deduce whether there are viruses in the analyzed air.

The scattering peak when there are biological molecules in the analyzed air sample must be substantially larger than the rest of the scattered light. This means that, if the light intensity received by each of the photodetectors arranged at various scattering angles is compared, at least one of such photodetectors receives scattered light whose intensity is several orders of magnitude greater than the intensity of the received scattered light in the rest of photodetectors, for example 100 or 1000 times higher.
3. Estimating the concentration of the biological molecules in the particles as a function of the amplitude of said peak in the intensity of the scattered light.

The inventors of the present application have discovered that the value of maximum intensity is related to the concentration of biological molecules in the analyzed air. Specifically, the greater the concentration of optically absorbing biological molecules in the particles present in the air sample, the greater the amplitude of the intensity peak emitted. Therefore, the amplitude of the intensity peak is proportional to the concentration of biological molecules 4. Estimating the size of the particles containing the biological molecules of interest as a function of the scattering angle corresponding to the position where said peak in the intensity of the scattered light was detected.

The inventors of the present application have found that the intensity peak appears at a particular scattering angle, thus being detected by the photodetector located at said position. Furthermore, the inventors of the present application have found that this angle is correlated to the size of the particles containing the biological molecules in question. Therefore, knowing the scattering angle of the photodetector that detects the intensity peak mentioned in the previous section, it is possible to determine the size of the particles that contain the biological molecules of interest.

In short, this procedure makes it possible to determine whether there are suspended particles in the analyzed air sample that contain a certain biological molecule of interest. For example, it is possible to project a beam of 255 nm monochromatic polarized light through the air sample placed in the test zone. Certain nucleotides characteristic of viruses present their maximum absorption at approximately 255 nm, so that if any of the photodetectors receives an intensity several orders of magnitude greater than the rest, for example 100 or more times greater, it is determined that effectively in the air sample there are particles containing nucleotides. In addition, depending on the intensity peak value detected by the photodetector, the concentration of nucleotides in the particles can be estimated. Finally, taking into account the angle at which the photodetector receiving the intensity peak is located, the size of the particles can be estimated. All this information makes it easier to characterize the biological agent present in the air sample, identifying whether it is a virus, etc.

Furthermore, by passing a continuous flow of air through the test area while maintaining the beam of monochromatic polarized light illuminating the test area, it is possible to detect the concentration of particles with certain characteristics in the air flow. For this, in a particularly preferred embodiment of the invention, the procedure further comprises the steps of:

To drive a known flow rate of air through the sample zone. As will be described later, any known device can be used for this, such as a pump, fan, or blower.

To count a number of pulses corresponding to intensity peaks that occur at a certain scattering angle and whose amplitude is within a certain interval. The scattering angle is chosen to correspond to the size of the particles to be detected, and the amplitude range is chosen to correspond to the concentration of biological molecules to be detected. Thus, each time particles of the size in question pass through the sample zone and with the concentration of biological molecules of interest within the interval in question, at the selected scattering angle, a peak intensity pulse is produced with a maximum at selected range. These pulses are identified and counted.

To estimate, from the number of pulses per unit time and the impelled air flow rate, the concentration of particles whose size and concentration of biological molecules correspond to the given scattering angle and amplitude. Specifically, it is sufficient to divide the number of pulses per unit time by the air flow rate to obtain the concentration of particles with the determined characteristics.

In another preferred embodiment, the method comprises simultaneously emitting towards the test area several monochromatic polarized light beams whose wavelengths essentially correspond to respective absorption maxima of various biological molecules of interest. In this case, some filters can be placed on the photodetectors to differentiate between the light intensity received corresponding to the dispersion of one and the other beams. The aforementioned data is obtained for a number of different biological molecules, thereby increasing the ability of the method to identify the biological agent present in the air sample.

A second aspect of the present invention is directed to a system for detecting biological agents suspended in the air in real time, which comprises the following elements:
  a) A monochromatic polarized light emitter, preferably a laser emitter, for emitting, towards a test zone comprising an air sample, a monochromatic polarized light beam whose wavelength corresponds essentially to an absorption maximum of a biological molecule of interest. In a preferred embodiment of the invention, the wavelength of the monochromatic polarized light beam emitted by the emitter ranges from 240 nm to 280 nm, even more preferably from 255 nm to 260 nm.
  b) A set of photoreceptors located in different positions corresponding to different scattering angles of the scattered light beam after its passage through the air sample. These photodetectors will receive the scattered light after passing through the air sample arranged in the test zone.
  c) A processing means connected to the photoreceptors, where the processing means is configured to:
    c1) To determine that there are particles in the air sample that contain the biological molecules of interest if the intensity of the scattered light received by the photoreceptors has a substantially higher peak than the rest of the scattered light.
    c2) To estimate the amount of said biological molecules as a function of the amplitude of the peak in the intensity of the scattered light.
    c3) To estimate the size of the particles containing said biological molecules as a function of the scattering angle corresponding to the position where the peak was detected in the intensity of the scattered light.

According to one embodiment, the system also comprises a pumping means that drives a flow of air to be analyzed towards the sampling zone. As described earlier in this document, this allows the concentration of particles having a given size and concentration of biological molecules to be estimated. Specifically, the number of pulses per unit of time corresponding to detected intensity peaks that occur at a scattering angle corresponding to the desired particle size and whose amplitude is within a certain interval corresponding to the desired concentration of biological molecules is counted. It is then enough to divide the number of pulses by the air flow to obtain the desired particle concentration.

According to one embodiment, the system comprises several monochromatic polarized light emitters for simultaneously emitting several monochromatic polarized light beams whose wavelengths essentially correspond to respective absorption maxima of various biological molecules of interest. In this case, the photodetectors can have filters capable of separating the received scattered light corresponding to each of the beams, for example, based on its wavelength. As mentioned above, this configuration would allow information about several types of biological molecules to be obtained simultaneously, improving the ability to identify the biological agent present in the sample.

According to another embodiment, the system further comprises a face mask provided with a conduit connected to the test zone for conducting exhaled air from a person to the test zone. This configuration is particularly aimed at the detection of viruses present in the human respiratory system, such as SARS-CoV-2.

DETAILED DESCRIPTION

An example of a system according to the present invention is described below with reference to the attached figures.

Figure 1:
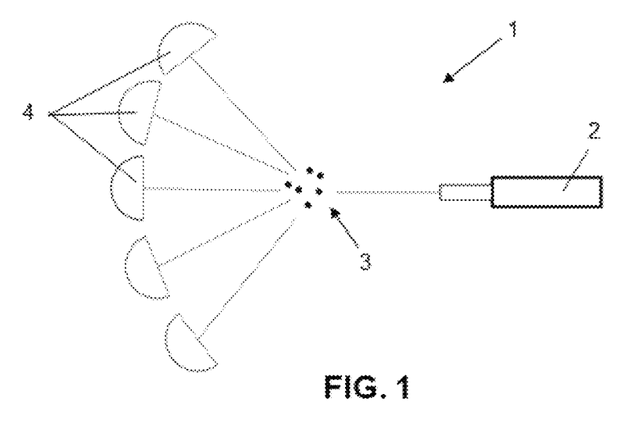
FIG. 1 shows a simplified diagram of an example of a biological agent detection system according to one embodiment.

As shown in FIG. 1, the system 1 comprises a laser emitter 2 that emits a beam of monochromatic polarized light towards a test area 3 containing a sample of the air to be analyzed. A set of photodetectors 4 are arranged at different angles relative to the test zone 3 to receive the scattered light after passing through the air contained in the test zone 3. The photodetectors 4 can also have a polarizing filter to make them selective to a specific state of polarized light.

Although not shown in detail in the figure, the test zone 3 can comprise an essentially closed container in which the air sample to be analyzed is housed. Alternatively, the test zone may be part of a duct through which the air to be tested passes continuously. In either case, the container or conduit must have transparent walls at least in the directions corresponding to the light beam emitted by the laser emitter 2 and to the position of the photodetectors 4 that receive the scattered light.

The angular characteristics of the Mie scattering are expressed by two intensity distribution functions (i1 and i2), which correspond to the intensities of polarized light in the directions perpendicular and parallel to the plane of FIG. 1. These functions form the basis of the Mie theory and are expressed as a function of:

Size parameter: $\alpha = 2\pi r/\lambda$, where r is the radius of the particle and $\lambda$ the wavelength of the light used.

Complex refractive index: m. (where the imaginary part is the absorption coefficient of light of that wavelength in the medium)

Angle of incidence of the primary wave: $\phi$

Thus, the angular distribution function of the scattered radiation intensity is expressed by:

$$\Phi(\alpha, m, \phi) = \left(\frac{\lambda^2}{4\pi^2}\right)\left(\frac{i1 + i2}{2}\right)$$

For a spherical and isotropic particle i1 and i2 are given by:

$$i1(\alpha, m, \phi) = \left|\sum_{n=1}^{\infty}\frac{2n+1}{n(n+1)}(a_n\pi_n + b_n\tau_n)\right|^2$$

$$i2(\alpha, m, \phi) = \left|\sum_{n=1}^{\infty}\frac{2n+1}{n(n+1)}(a_n\tau_n + b_n\pi_n)\right|^2$$

Being $$a_n = \frac{\alpha\Psi_n(\alpha)\Psi'_n(m\alpha) - m\alpha\Psi'_n(\alpha)\Psi_n(m\alpha)}{\alpha\varepsilon_n(\alpha)\Psi'_n(m\alpha) - m\alpha\varepsilon'_n(\alpha)\Psi_n(m\alpha)}$$

$$b_n = \frac{m\alpha\Psi_n(\alpha)\Psi'_n(m\alpha) - \alpha\Psi'_n(\alpha)\Psi_n(m\alpha)}{m\alpha\varepsilon_n(\alpha)\Psi'_n(m\alpha) - \alpha\varepsilon'_n(\alpha)\Psi_n(m\alpha)}$$

$$\pi_n = \frac{1}{\sin\phi}P_n^1(\cos\phi)$$

$$\tau_n = \frac{d}{d\phi}P_n^1(\cos\phi)$$

$\Psi_n$ and $\varepsilon_n$ are the Riccati-Bessel functions, which can be expressed as:

$$\Psi_n(m\alpha) = zj_n(z)$$

$$\varepsilon_n(\alpha) = zj_n(z) - izY_n(z)$$

where $j_n$ and $Y_n$ are spherical Bessel functions.

Therefore, in the event that the particles contain molecules with absorption at a certain wavelength, the imaginary part of the refractive index will be greater than if these molecules are not present. As a consequence, in these cases there will be a peak of light intensity scattered at certain angles.

The case of nucleotides, which have an absorption zone for wavelengths from 240 to 280 nm, is known. Reference can be made, for example, to the 1995 article by Jürgen H. Fischer entitled "*Specific detection of nucleotides, creatine phosphate, and their derivatives from tissue simple in a simple, isocratic, cecycling, low-volume system*" or the article by Alison Rodger, 2013 entitled "*UV absorbance spectroscopy of biological macromolecules*". This property is also known for other types of biological molecules, such as some amino acids. Tryptophan, for example, has its absorption maximum at 280 nm. Thus, in the present invention, a wavelength is chosen that corresponds to the position of the absorption maximum of the biological molecule to be detected.

Thus, small particles with a high content of nucleotides, as occurs in many pathogenic and infectious biological agents such as RNA or DNA viruses, will produce a Mie scattering of polarized light that includes a peak at a certain angle. For example, if a beam of polarized light with a wavelength ranging from 240 nm to 280 nm is used on an air sample in which a nucleotide-containing virus is suspended, there will be an increase in scattering relative to a nucleotide-containing virus. particle of the same size that did not contain those nucleotides. The dispersion will also preferably occur at a certain angle that depends on the size of the particle.

Figure 2:
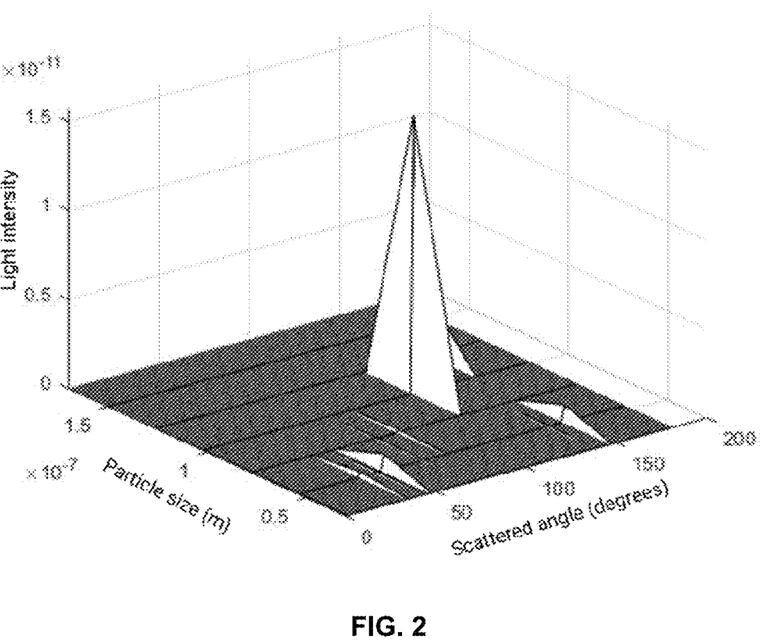
FIG. 2 shows a plot of the intensity of 255 nm light scattered by a nucleotide-containing particle with absorption at that wavelength as a function of size and scattering angle.

This situation is shown in FIG. 2, which represents the light intensity received by the photodetectors 4 as a function of the size of the particles present in the sample zone 3 and the angle of dispersion corresponding to the photodetector 4 that receives this light intensity. In this specific case, a monochromatic polarized light of 255 nm wavelength has been used to illuminate an air sample in which there are suspended virus particles of 0.1 microns ($10^{-7}$ m) which, as is known, is essentially made up of DNA or RNA contained in a capsule. The light beam passes through the particles present in the air sample, being scattered in different directions and captured by several photodetectors 4. However, as can be easily seen in the graph, the photodetector 4 located at an angle of 110° receives a light signal several orders of magnitude more intense than the rest of the photodetectors 4 located at other angles. This allows us to deduce that, indeed, there are biological agents in the air sample, such as a virus, which contains guanine. Furthermore, since the peak occurs specifically at an angle of 110°, the particle size of the biological agent is estimated to be approximately 0.1 micron. Finally, the concentration of guanine in the sample is also estimated as a function of the amplitude of the peak, which here is approximately 1.5×10-11. It is an intensity per angle unit subtended by the photoreceptor and which is also proportional to the intensity of the light source multiplied by the factor $\phi$ described above.

Figure 3:
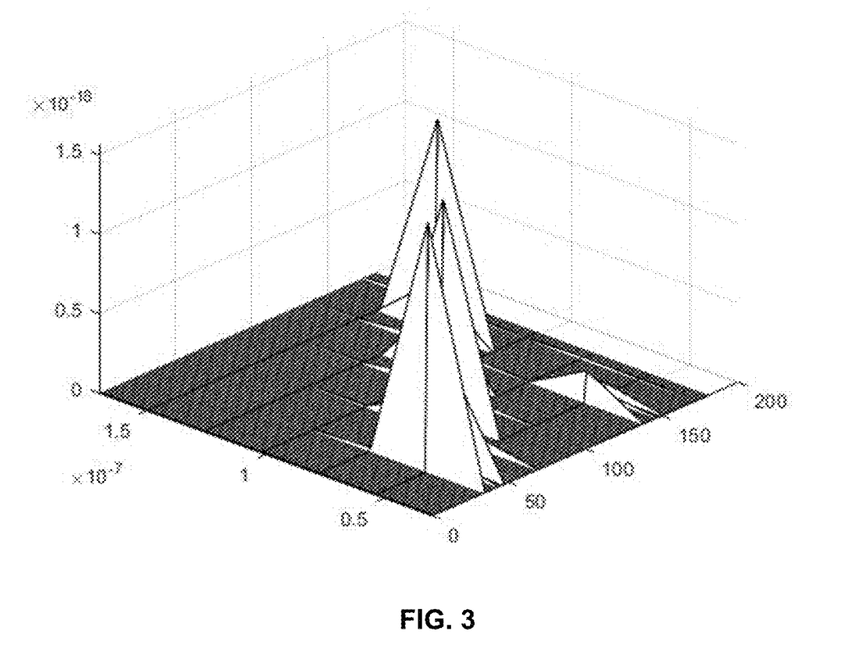
FIG. 3 shows a plot of the intensity of 255 nm light scattered by a particle containing no nucleotides as a function of size and scattering angle.

FIG. 3 shows a situation in which the method of the invention is applied to an air sample that does not contain biological material of any kind. For example, the air sample may contain only dust particles or the like. This air sample is illuminated with a beam of 255 nm monochromatic polarized light. In the first place, the graph shows that there is no peak of intensity substantially greater than the rest. Three peaks of approximately the same magnitude can be seen, which, moreover, are approximately seven orders of magnitude smaller than the peak shown in FIG. 2 (note the different intensity scale in both graphs). Therefore, it can be determined that the analyzed air sample does not contain biological material whose absorption peak is near 255 nm, such as guanine and other nucleotides. Secondly, it can be seen in the graph that the three peaks obtained are located in positions corresponding to scattering angles of 40°, 70° and 160°. Therefore, the particles present in the sample are determined to have three predominant sizes.

In this example, a processing means 7 (shown in FIG. 4) is connected to the photodetectors 4 to perform the necessary calculations. This processing means can, in principle, be of any suitable type, including a computer, mobile phone, or tablet, as well as a processor, controller, FPGA, DSP, ASIC, or others.

This procedure can be carried out to detect different types of biological molecules simultaneously. To do this, it is enough to illuminate the sample with several juxtaposed beams of monochromatic polarized light corresponding to different wavelengths. The light scattered by the sample is received by the photodetectors which, by means of polarizing filters, will be able to separate the light scattered by one or another beam. This allows the presence of several selected biological and/or non-biological molecules to be detected simultaneously, improving the system's ability to identify the biological material detected.

Figure 4:
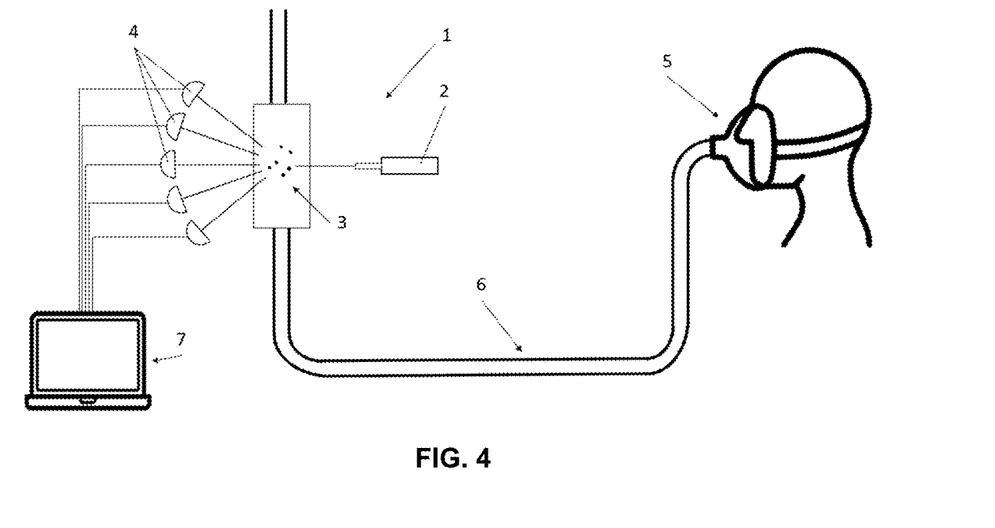
FIG. 4 shows an embodiment of a biological agent detection system provided a mask coupled to the test area by use of a conduit.

FIG. 4 additionally shows a face mask 5 provided with a conduit 6 connected to the test area 3 to conduct air exhaled by a person to the test area 3 of the device.

Additional embodiments are disclosed in the clauses that follow.

Clause 1. A procedure for real time detection of biological agents suspended in the air, characterized in that it comprises the following steps:

To emit, towards a test area 3 comprising an air sample, a monochromatic polarized light beam whose wavelength essentially corresponds to an absorption maximum of a biological molecule;

To receive, in different positions corresponding to different scattering angles, the scattered light beam after its passage through the air sample;

To determine that particles containing the biological molecules of interest are present in the air sample if the intensity of the scattered light has a substantially higher peak than the rest of the scattered light;

To estimate the concentration of the biological molecules in the particles as a function of the amplitude of the peak in the intensity of the scattered light; and To estimate the size of the particles containing the biological molecules of interest as a function of the scattering angle corresponding to the position where the peak was detected in the intensity of the scattered light.

Clause 2. The procedure according to clause 1, further comprising the steps of:

To drive a known flow rate of air through the sample zone;

To count a number of pulses corresponding to intensity peaks that occur at a certain scattering angle and whose amplitude is within a certain interval; and To estimate, from the number of pulses per unit of time and the flow of air driven, the concentration of particles whose size and concentration of biological molecules correspond to said dispersion angle and amplitude determined.

Clause 3. The procedure according to any of the preceding clauses, which comprises simultaneously emitting towards the test area 3 containing the air sample several beams of monochromatic polarized light whose wavelengths essentially correspond to the respective absorption maxima of various biological molecules of interest.

Clause 4. The procedure according to any of the preceding clauses, wherein the wavelength of the at least one beam of monochromatic polarized light ranges from 240 nm to 280 nm.

Clause 5. The procedure according to clause 4, wherein the wavelength of at least one monochromatic polarized light beam is approximately ranges from 255 nm to 260 nm.

Clause 6. Procedure according to any of the preceding clauses, where the at least one beam of monochromatic polarized light is a laser beam.

Clause 7. A system 1 to detect biological agents suspended in the air in real time, characterized in that it comprises:

a monochromatic polarized light emitter 2 to emit, towards a test area 3 comprising an air sample, a monochromatic polarized light beam whose wavelength essentially corresponds to an absorption maximum of a biological molecule of interest;

a set of photoreceptors 4 located in different positions corresponding to different scattering angles of the scattered light beam after its passage through the air sample; and a processing medium 7 connected to the photoreceptors, wherein the processing medium is configured to:

determine that there are particles in the air sample that contain the biological molecules of interest if the intensity of the scattered light received by the photoreceptors 4 has a substantially higher peak than the rest of the scattered light;

estimate the concentration of the biological molecules in the particles as a function of the amplitude of the peak in the intensity of the scattered light; and/or to estimate the size of the particles containing the biological molecules of interest as a function of the scattering angle corresponding to the position where the peak was detected in the intensity of the scattered light.

Clause 8. The system 1 according to clause 7, which also comprises a pumping means that drives a flow of air to be analyzed towards the sampling area 3, which allows estimating, from the flow of air driven and the number of pulses per time unit that correspond to intensity peaks that occur at a given scattering angle and whose amplitude is within a given interval, the concentration of particles whose size and concentration of biological molecules correspond to the scattering angle and certain amplitude.

Clause 9. The system 1 according to any of clauses 7-8, comprising several emitters 2 of monochromatic polarized light to emit simultaneously towards the test area 3 containing the air sample several beams of monochromatic polarized light whose wavelengths essentially correspond to respective absorption maxima of various biological molecules of interest.

Clause 10. The system 1 according to any of clauses 7-9, further comprising a face mask 5 provided with a conduit 6 connected to the test zone 3 to conduct air exhaled by a person to the test zone 3.

Clause 11. The system 1 according to any of clauses 7-10, where the emitter 2 of monochromatic polarized light is a laser emitter.

Clause 12. The system 1 according to any of clauses 7-11, where the wavelength of the monochromatic polarized light beam emitted by the emitter 2 ranges from 240 nm to 280 nm.

Clause 13. The system 1 according to clause 12, where the wavelength of the polarized light beam emitted by the emitter 2 ranges from 255 nm to 260 nm.

What is claimed is:

1. A method for real-time detection of a first biological agent of interest suspended in air, the method comprising:

emitting towards a test area containing an air sample a first monochromatic polarized light beam having a first wavelength corresponding to an absorption maximum of the first biological agent;

receiving in a plurality of photodetectors arranged at different angles relative to the test area at least a portion of the first monochromatic polarized light beam in the form of scattered light after passing through the air sample in the test area;

for each of the plurality of photodetectors, determining an intensity of the scattered light;

comparing the intensity of the scattered light among the plurality of photodetectors to determine whether the intensity of the scattered light of one of the plurality of photodetectors has a substantially higher peak than the intensity of the scattered light received in the other of the plurality of photodetectors;

determining the air sample contains the first biological agent upon determining the intensity of scattered light of the one of the plurality of photodetectors has a substantially higher peak than the intensity of the scattered light received in the other of the plurality of photodetectors;

estimating a concentration of the first biological agent in the air sample as a function of an amplitude of the substantially higher peak; and estimating a size of the first biological agent as a function of a scattering angle corresponding to a position of the substantially higher peak.

2. The method according to claim 1, further comprising simultaneously emitting towards the air sample a second monochromatic polarized light beam having a second wavelength different from the first wavelength corresponding to an absorption maximum of a second biological agent.

3. The method according to claim 2, where each of the first and second monochromatic polarized light beams is a laser beam.

4. The method according to claim 2, further comprising receiving in the plurality of photodetectors at least a portion of the second monochromatic polarized light beam in the form of scattered light after passing through the air in the test area, each of the plurality of photodetectors having polarizing filters configured to separate the received scattered light associated with the first and second monochromatic polarized light beams.

5. The method according to claim 1, wherein the first wavelength ranges from 240 nm to 280 nm.

6. The method according to claim 5, wherein the first wavelength ranges from 255 nm to 260 nm.

7. The method according to claim 1, wherein each of the first wavelength and second wavelength is ranges from 240 nm to 280 nm.

8. The method according to claim 7, wherein each of the first wavelength and second wavelength ranges from 255 nm to 260 nm.

9. The method according to claim 1, where the first monochromatic polarized light beam is a laser beam.

10. A method for real-time detection of a biological agent of interest suspended in an air flow in a test area, the method comprising:

emitting towards the air flow in the test area a monochromatic polarized light beam having a wavelength corresponding to an absorption maximum of the biological agent;

receiving in a plurality of photodetectors arranged at different angles relative to the test area at least a portion of the monochromatic polarized light beam in the form of scattered light after passing through the air flow in the test area;

for each of the plurality of photodetectors, determining an intensity of the scattered light;

repeatedly comparing the intensity of the scattered light among the plurality of photodetectors at a given time interval to determine whether the intensity of the scattered light of one of the plurality of photodetectors has a substantially higher peak than the intensity of the scattered light received in the other of the plurality of photodetectors;

counting the number of substantially higher peaks detected that occur at a certain scattering angle and whose amplitude is within a certain interval; and based on the counted number of substantially higher peaks and the rate of air flow, estimating a concentration of the biological agent in the air flow.

11. The method according to claim 10, wherein the wavelength ranges from 240 nm to 280 nm.

12. The method according to claim 11, wherein the wavelength ranges from 255 nm to 260 nm.

13. The method according to claim 11, where the monochromatic polarized light beam is a laser beam.

14. A system for detecting a biological agent suspended in air in real-time, the system comprising:
　a first light emitter that is configured to emit a first monochromatic polarized light beam towards an air sample located in a test area, the first monochromatic polarized light beam having a first wavelength that corresponds to an absorption maximum of the biological agent;
　a plurality of photodetectors arranged at different angles relative to the test area at least a portion of the first monochromatic polarized light beam, the plurality of photodetectors being located to receive scattered light after the first monochromatic polarized light beam passes through the air sample in the test area; and
　a computer processor configured to receive data from the plurality of photodetectors to:
　　for each of the plurality of photodetectors, determine an intensity of the scattered light;
　　compare the intensity of the scattered light among the plurality of photodetectors to determine whether the intensity of the scattered light of one of the plurality of photodetectors has a substantially higher peak than the intensity of the scattered light received in the other of the plurality of photodetectors;
　　determine the air sample contains the first biological agent upon determining the intensity of scattered light of the one of the plurality of photodetectors has a substantially higher peak than the intensity of the scattered light received in the other of the plurality of photodetectors;
　　estimate a concentration of the first biological agent in the air sample as a function of an amplitude of the substantially higher peak; and
　　estimate a size of the first biological agent as a function of a scattering angle corresponding to a position of the substantially higher peak.

15. The system according to claim 14, further comprising an air blower for introducing air into the test area.

16. The system according to claim 14, where the first light emitter is a laser emitter.

17. The system according to claim 14, wherein the wavelength of the first monochromatic polarized light beam ranges from 240 nm to 280 nm.

18. The system according to claim 17, wherein the wavelength of the first monochromatic polarized light beam ranges from 255 nm to 260 nm.

19. The system according to claim 14, further comprising a face mask provided with a conduit connected to the test area to conduct air exhaled by a person to the test area.

20. The system according to claim 14, further comprising a second light emitter that is configured to simultaneously emit towards the test area a second monochromatic polarized light beam having a second wavelength different from the first wavelength corresponding to an absorption maximum of a second biological agent.

\* \* \* \* \*